United States Patent
Trueman et al.

(10) Patent No.: US 6,866,106 B2
(45) Date of Patent: *Mar. 15, 2005

(54) FLUID DRILLING SYSTEM WITH FLEXIBLE DRILL STRING AND RETRO JETS

(75) Inventors: Robert Trueman, Karana Downs (AU); Timothy Gregory Hamilton Meyer, Highgate Hill (AU); Matthew Stockwell, Cannon Hill (AU)

(73) Assignees: University of Queensland, Queensland (AU); Commonwealth Scientific and Industrial Research Organization, ACT (AU); BHP Coal Pty. Ltd., Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/237,255

(22) Filed: Sep. 4, 2002

(65) Prior Publication Data

US 2003/0164253 A1 Sep. 4, 2003

Related U.S. Application Data

(63) Continuation of application No. 09/738,883, filed on Dec. 15, 2000, now Pat. No. 6,470,978, which is a continuation of application No. 09/091,048, filed on Jun. 8, 1998, now abandoned, which is a continuation of application No. PCT/AU96/00783, filed on Dec. 5, 1996.

(30) Foreign Application Priority Data

Dec. 8, 1995 (AU) ............................................. PN7031

(51) Int. Cl.[7] .............................. E21B 7/08; E21B 7/18
(52) U.S. Cl. ............................ 175/67; 175/424; 299/17
(58) Field of Search ............................ 299/17; 175/61, 175/62, 67, 424

(56) References Cited

U.S. PATENT DOCUMENTS

| 1,435,144 A | * 11/1922 | Bignell ...................... 405/248 |
| 1,660,999 A | 2/1928 | MacDonell |
| 1,865,853 A | 7/1932 | Granville |
| 2,282,431 A | 5/1942 | Smith et al. |
| 2,516,421 A | 7/1950 | Robertson |

(List continued on next page.)

FOREIGN PATENT DOCUMENTS

| DE | 30 12 482 A1 | 10/1981 |
| FR | 2 493 907 | 5/1982 |
| GB | 2 289 298 A | 11/1995 |
| JP | 06346676 A | 12/1994 |
| RU | 1093062 | 8/1994 |
| WO | WO 95/09963 | 4/1995 |
| WO | WO 97/21900 | 6/1997 |
| WO | WO 03/042491 A1 | 5/2003 |

OTHER PUBLICATIONS

Maramzin, A. V., "Automation and Mechanization of Tripping Processes (Review of foreign patents)", pp. 83–84, undated.

International Search Report for International Application No. PCT/AU 98/00422; mailed Jul. 21, 1998; Applicants: The University of Queensland et al.; 4 pages.

Derwent Abstract Accession No. 57667B/46, Class Q49, Su 649815, A (UKR Coal Hydr Minin) Feb. 28, 1979.

*Primary Examiner*—Sunil Singh
(74) *Attorney, Agent, or Firm*—Perkins Coie LLP

(57) ABSTRACT

A self-advancing drilling system comprising a drilling apparatus, the drilling apparatus having at least one leading fluid cutting nozzle, an advancing device on the drilling apparatus to provide forward movement to the drilling apparatus, the drilling system further comprising a drill string formed from recoverable flexible hose and a steering device having at least one jet nozzle.

19 Claims, 4 Drawing Sheets

U.S. PATENT DOCUMENTS

| | | | |
|---|---|---|---|
| 3,191,697 A | 6/1965 | Haines | |
| 3,844,362 A | 10/1974 | Elbert et al. | |
| 3,858,398 A | 1/1975 | Van Weele | |
| 3,873,156 A | 3/1975 | Jacoby | |
| 3,874,733 A | 4/1975 | Poundstone et al. | |
| 3,881,775 A | 5/1975 | McPherson et al. | |
| 3,887,021 A | 6/1975 | Elbert | |
| 3,917,007 A * | 11/1975 | Tsiferov | 175/14 |
| 4,007,797 A | 2/1977 | Jeter | |
| 4,273,193 A | 6/1981 | Tompkins | |
| 4,437,706 A | 3/1984 | Johnson | |
| 4,440,242 A | 4/1984 | Schmidt et al. | |
| 4,497,381 A | 2/1985 | Dickinson, III et al. | |
| 4,503,918 A | 3/1985 | Bergkvist et al. | |
| 4,527,639 A | 7/1985 | Dickinson, III et al. | |
| 4,640,362 A | 2/1987 | Schellstede | |
| 4,674,579 A | 6/1987 | Geller et al. | |
| 4,714,118 A | 12/1987 | Baker et al. | |
| 4,765,416 A * | 8/1988 | Bjerking et al. | 175/71 |
| 4,773,113 A | 9/1988 | Russell | |
| 4,826,087 A | 5/1989 | Chinery | |
| 4,850,440 A * | 7/1989 | Smet | 175/67 |
| 4,930,586 A | 6/1990 | Turin et al. | |
| 4,991,667 A | 2/1991 | Wilkes, Jr. et al. | |
| 5,179,753 A | 1/1993 | Flaherty et al. | |
| 5,197,783 A | 3/1993 | Theimer et al. | |
| 5,255,750 A | 10/1993 | Wilkes, Jr. et al. | |
| 5,288,173 A | 2/1994 | Jenne et al. | |
| 5,413,184 A | 5/1995 | Landers | |
| 5,439,066 A | 8/1995 | Gipson | |
| 5,814,162 A * | 9/1998 | Barrett et al. | 134/22.12 |
| 5,853,056 A * | 12/1998 | Landers | 175/424 |
| 5,899,283 A | 5/1999 | Cox | |
| 5,950,743 A | 9/1999 | Cox | |
| 6,012,536 A * | 1/2000 | Puttmann et al. | 175/21 |
| 6,109,370 A * | 8/2000 | Gray | 175/61 |
| 6,231,270 B1 * | 5/2001 | Cacossa | 405/248 |
| 6,263,984 B1 * | 7/2001 | Buckman, Sr. | 175/67 |
| 6,470,978 B2 | 10/2002 | Trueman et al. | |
| 6,530,439 B2 * | 3/2003 | Mazorow | 175/89 |

* cited by examiner

FLUID DRILLING SYSTEM WITH FLEXIBLE DRILL STRING AND RETRO JETS

This application is a continuation of U.S. application Ser. No. 09/738,883, filed Dec. 15, 2000, which is incorporated by reference herein, which has now issued as U.S. Pat. No. 6,470,978, and which is a continuation of U.S. application Ser. No. 09/091,048, filed on Jun. 8, 1998 now abandoned, which is a continuation of PCT/AU96/00783, filed Dec. 5, 1996.

FIELD OF THE INVENTION

This invention relates to a fluid drilling system and particularly relates to a self-advancing fluid drilling system which can be used in a variety of mining applications, including but not limited to, drilling into coal seams, to drain methane gas.

BACKGROUND

Fluid drilling systems are known and use water under high pressure to cut solids such as soft rock, coal and the like. These water jet drilling systems are finding greater acceptance in the mining industry and can be used instead of the traditional mechanical cutting heads.

The known water jet drilling systems all have a cutting apparatus advanced by forces transmitted along a rigid drill string or in one instance by fluid pressure exerted on a piston type arrangement. The cutting apparatus has one or more water jet cutting nozzles on a leading portion of the apparatus.

Conventionally, in order to cut a circular hole, the rigid drill string is rotated thereby sweeping the forward cutting jets through a circular path.

More recently a more successful arrangement has been developed whereby the cutting jets alone are rotated by means of a swivel head powered by the thrust from the cutting jets, with all other parts of the drill stem leading to the cutting head being stationary. The apparatus is advanced by pushing on the rigid drill string with the rotating fluid cutting head cutting a hole in the solid.

More recently, a water jet drilling system has been developed which is effective in drilling in-seam boreholes of up to 300 m length or more with a rigid drill string. The major features of this drilling nozzle are:
a commercially available Woma FR47 high speed self-rotating water jet nozzle as the main cutting component,
a stepless shroud cage to prevent the Woma FR47 nozzle from stalling (stop spinning),
a bent sub member to control the borehole trajectory,
a retro sub member to provide sufficient flow to flush the relatively large cuttings from the hole,
a nozzle cross over sub to connect the Woma FR47 nozzle to the retro sub member and the retro sub member to the drill string.

To advance the cutting apparatus and to provide the cutting fluid to the nozzle, drill rods of 3 m length, designed to withstand internal pressures of up to 1000 bar, were used. These drill rods were used as a conduit for the required supply of high pressure water to the drilling nozzle. (The rods were also used as a conduit for the required supply of high pressure water to the drilling nozzle). The rods were also used in association with a drilling rig to push or advance the nozzle into the borehole. To facilitate the removal of the cutting debris from the borehole, rearwardly facing flushing nozzles (or retro jets) were used. A high pressure water pump capable of a maximum pressure of 650 Bar at a flow rate of 160 liters per minute was used for this work.

In this more recent arrangement, the drilling technique involved the following steps:
align the drill rig to the desired borehole direction,
attach the Woma FR47 nozzle to the high pressure drill rods (the first 10 meters of borehole were drilled without the bent sub and retro assembly members. This is done to avoid unnecessary spray back from the flushing jets on the retro sub), after collaring 10 meters of borehole the drill string is withdrawn from the hole and the bent sub and retro assembly members attached behind the Woma FR47 nozzle, the nozzle assembly and drill string are re-inserted to the bottom of hole (BOH) and drilling continued, the nozzle assembly being advanced by pushing on the drill string with the rig.

A recognised advantage of fluid drilling systems is their propensity for Round the Corner or Ultra-Short Radius Drilling. These methods typically involve drilling horizontal holes radiating out from a vertical well. To allow Round the Corner Drilling, it is known to make the drill string tube up in steel segments each 45 cm long and hinged on the top surface. A drive chain is welded along the length of the string. As the segments come down the vertical well, they are disconnected on their lower side and are able to rotate around a drive cog at the bottom of the vertical well. Thus, the drill string would feed down the vertical well as a rigid unit and would also feed into the horizontal hole as a rigid unit.

The water cutting nozzle was powered by pressurised water which was fed through a high pressure hose. The high pressure hose either extended through the rigid drill string, or to one side of the drill string.

One method of Ultra-Short Radius Drilling involves a fluid drilling apparatus attached to a length of coiled tubing. The fluid drilling apparatus and coiled tubing are fed through a whipstock assembly which bends the tubing through an ultra-short radius bend (0.3 m radius). The tubing is thereby deflected laterally away from the vertical well by plastically deforming the tubing through a series of guides and rollers. The coiled tubing is used to supply the high pressure cutting fluid to the fluid drilling apparatus. The fluid drilling apparatus is forced into the formation to be drilled by means of a complicated piston arrangement which utilises the high pressure of the cutting fluid.

A difficulty with water cutting systems is ensuring that the nozzle assembly remains in the desired horizon as the apparatus is advanced by the rigid drill string. It is noted with conventional systems that there is a tendency for the cutting apparatus to drop relative to an horizon as it is advanced.

While not wishing to be bound by theory, it appears that the drop is caused by the drill string being rigid, or by the drill string otherwise being predominant in the advancement of the nozzle assembly.

To steer these devices, a bent sub is used and the rigid drill string is rotated to rotate the orientation of the bent sub and this provides a measure of steering to the system.

Drill strings formed from coiled tubing are known. The coiled tubing allows the drill string to exhibit some degree of flexibility. However the coiled tubing allows only a restricted amount of flex, and it is found that if the coiled tubing is forced around a whipstock, the tubing goes past its elastic limit which means that it is difficult to retrieve. The tubing must be cut-off electrochemically, or by some other means and therefore does not function as a flexible hose.

International Patent Application WO 95/09963 describes a drilling system. In this system a first drill string is pushed down a borehole and deflected horizontally via an elbow. The first drill string has a mechanical ball cutter and the drill string is rotated to rotate the ball cutter. This drill string is then removed, and a second flexible drill string is inserted down the bore hole and through the elbow.

The second drill string does not rotate and terminates with a relatively low pressure fluid cutter, cutting at about 3000–4000 psi. The fluid cutter slowly blasts a bore in the surrounding strata. There appears to be no method to advance the drill string into the horizontal bore other then by the weight of the drill string in the vertical or by conventional pushing on the drill string. The cutter has a more or less conventional low pressure retro jet assembly (about 3000–4000 psi) which functions to flush away the cuttings. The stated angle of the retro jets (45°) is consistent with a flushing action but at this angle the jets do not function to provide any meaningful forward thrust. In fact, it appears that the jets, if anything, may have an additional function to balance the kick back caused by the front non rotating nozzles, such that advancement is caused by the weight of the drill string.

As there is no advancement mechanism other then by the weight of the drill string, the fluid cutter advances very slowly with a stated cutting rate being 60 m in 6–10 hours even in soft rock.

As the drill string appears to effect the forward movement of the cutter, the problem of drop in the cutting angle may still occur, a problem found with rigid drill strings.

With no advancement means other then the weight of the drill string being apparent, there is a high probability that extended horizontal drilling will cause the flexible drill string to adopt what is known as "helical lock up" which is when the drill string can no longer be advanced by pushing on the drill string. This effect is probably why the horizontal hole lengths in the examples were limited to about 60 m.

In the examples, the drill string is a coiled steel tube of smaller than usual diameter (12.5 mm) to provide it with sufficient flexibility. With the small diameter tube, only small volumes of low pressure water can pass to the fluid cutter.

In draining methane from a coal seam, it is essential for the sake of efficiency to not change the permeability of the coal. Any reduction in the permeability will adversely effect methane drainage into the cut bore from the surrounding coal. It is known that surfactants reduce coal permeability and therefor, for drilling drainage holes in coal seams, the drilling system described above would not be suitable as surfactants are required.

SUMMARY

In the present invention, a system has been developed whereby the rigid drill string is replaced by a flexible drill string which is not intended to advance the nozzle assembly. We find that with a flexible drill string the cutting device remains in the same horizon. Our flexible drill string can accommodate high pressure fluid (10000–20000 psi) and has a reduced ability, or no ability to push or advance the cutting apparatus. Therefore the present invention also includes a self-advancing system which, in one form, may be in the form of retro jets having a configuration and sufficient thrust to provide advancement to the cutting apparatus.

A major advantage of using a high pressure flexible hose as the drill string is that it can be fed and retracted continuously from a drum. This eliminates the requirement to continuously add and take off rigid drill rods. Significant productivity gains are therefore possible with this technology. Although coiled steel tubing which is known technology can be used in a similar way, the capital cost of the tubing and winches are considerably greater than for this invention.

Additionally complicated and expensive ways are required to advance it in to the borehole. With this invention, the cutting assembly and flexible drill string can be advanced relatively simply and cheaply.

The flexibility of the drill string also makes the invention applicable to directional drilling. Directional drilling relates to situations where there are benefits in changing the direction of a drill hole in a controlled manner. In particular the high pressure hose is capable of being turned relatively easily through an ultra-short-radius which is defined as 0.6 m or less. The only other known technology capable of achieving this is again coiled tubing which has a significant greater capital cost associated with it as mentioned earlier. Additionally coiled tubing can only be made to turn through an ultra-short-radius by forcing the steel tubing past the elastic limit of the material. The strains involved seriously reduces the working life of the tubing which typically means that the section of tubing that passes through the ultra-short-radius is not retracted and complicated methods have to be used to sever it, including mechanical and electro chemical shearing devices. This adds significantly to costs. With this invention the flexible drill string can be retracted and re-used without the working lifetime of the high pressure hose being unduly affected. A further disadvantage of coiled tubing for directional drilling in coal is that if not retracted, the tubing can represent a safety hazard for the subsequent mining of the coal by underground methods. The chemicals used to sever the tubing may also adversely affect the permeability of the coal seam.

It is an object of the invention to provide a drilling system which may overcome the abovementioned disadvantages or provide the public with a useful or commercial choice.

In one form, the invention resides in a self-advancing drilling system comprising a drilling apparatus, the drilling apparatus having at least one leading fluid cutting nozzle, means on the drilling apparatus to provide forward movement to the drilling apparatus, and a drill string formed from a recoverable flexible hose.

Thus, by doing away with the rigid drill string, and providing a self-advancing mechanism preferably in the form of one or more retro jets, an efficient drilling system is obtained.

The flexible hose may function only as the drill string, but it is preferred that the flexible hose also functions as a conduit for the fluid to power the cutting nozzle and the retro jets. It is envisaged that separate further hoses may be provided as a conduit for the fluid, but at this stage, it is preferred that the drill string itself also functions as the fluid hose. The hose should be able to withstand high pressures of 10000–20000 psi.

The drilling apparatus itself may comprise a number of interconnected sub members.

A leading portion of the drilling apparatus may include a rotating high pressure nozzle. A suitable nozzle is a Woma FR47 nozzle which is available commercially. This nozzle includes forward cutting jets and side reaming jets and can be used with nozzle pressures of between 10000–20000 psi and typically 10000–15000 psi.

The nozzle may be mounted for rotation within a protective housing. The protective housing may comprise a rear tubular portion and a forward open cage portion. The cage portion can protect the nozzles and reduce the incident of a nozzle striking the solid as the nozzle rotates.

The cage may be stepped with the location of the step being immediately behind the reaming jets. The step can aim the reaming jets onto protrusions on the borehole wall which catch on the step and prevent the nozzle from advancing. The reaming jets may then be able to remove the protrusions and hence allow the cutting apparatus to advance.

The apparatus does not require a bent sub member as the flexible hose may not be suitable for controlling the orientation of the bent sub member.

Preferably, at least one retro jet is provided which may form part of a retro jet sub member. The retro jet sub member can be positioned adjacent a rear portion of the cutting apparatus. This sub member may have four retro jets comprising rearwardly pointing nozzles, and the retro jets may be equally spaced about the sub member. The retro jets provide forward thrust, and thus self advancement to the drilling apparatus. The jets typically function at 10000–20000 psi and the number and size of the jets can be varied to provide a net forward thrust to the apparatus.

To function efficiently as "thrust" jets, the jet nozzles are preferably at a small angle to longitudinal axis of the apparatus. Angles of 0°–30° are preferred, with an angle of about 5° being particularly preferred as this angle causes "thrust" water to clear the attached flexible hose (and not cut into it), while still having an acceptable rearward thrust angle.

The cutting apparatus can be steered by a steering means. One form of the steering means comprises fluid passing through the retro jet nozzles which can be selectively deflected by a deflecting assembly. The deflecting assembly can thereby assist in steering the cutting apparatus. The deflecting assembly may comprise a deflecting member which can be moved selectively into and out of the fluid jet stream to deflect the stream. Suitably, the deflecting member comprises a protrusion, or like member on a ring, the ring extending about the retro sub member. Rotation of the ring can cause the deflecting member to selectively pass into and out of a fluid jet stream. The ring may be rotated by an actuator which may be located within the cutting apparatus.

The deflecting assembly may form part of a guiding system for steering the cutting apparatus through a solid body such as a coal seam. The guiding system can be designed to provide a continuous real time indication of the attitude of the cutting apparatus and can allow an operator to steer the apparatus by computer control on the surface. The guiding system can comprise the following components:
(a) a sensing instrument which determines the location of the cutting apparatus in 3-D space,
(b) a single core wireline to transmit information between the cutting apparatus and the surface,
(c) a computer to calculate and display information relating to the trajectory of the cutting apparatus, and
(d) a steering mechanism which may comprise the deflecting assembly as described above.

BRIEF DESCRIPTION OF THE DRAWINGS

An embodiment of the invention will be described with reference to the following drawings in which.

DETAILED DESCRIPTION

Figure 9:
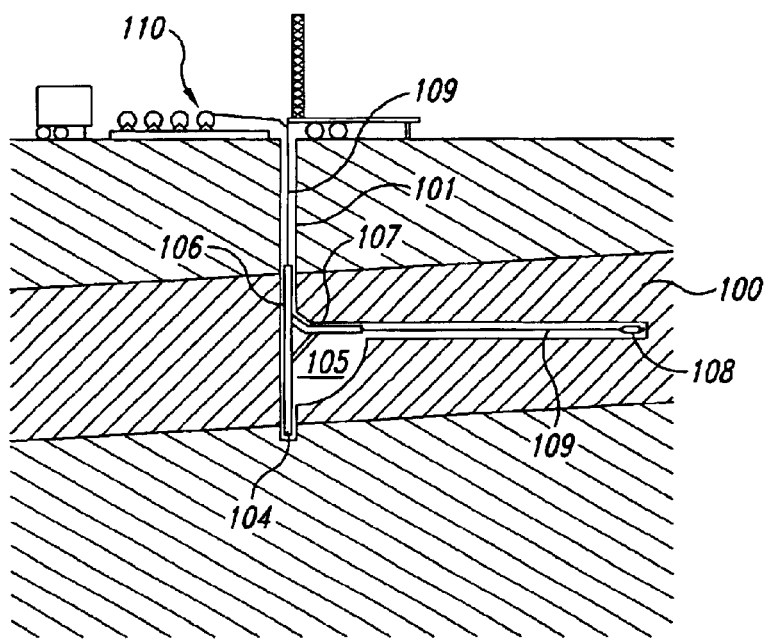
FIG. 9 illustrates generally, the fluid drilling system in use.

Referring to the drawings and initially to FIG. 9, there is shown diagrammatically a system for cutting a substantially horizontal passage into a coal seam 100. FIG. 9 shows a vertical bore 101 extending through the coal seam. A whipstock apparatus 104 is positioned in the bore and in a pre-formed cavity 105. Whipstock apparatus 104 has a main body 106 sized to allow the whipstock to be inserted into the bore. An extendible arm 107 is attached to the main body portion, and the arm can be hydraulically erected to adopt a horizontal orientation (other angles are also possible).

The fluid drilling apparatus 108 which is the subject of the current application can be housed in the arm 107, such that when the arm is erected, the apparatus can start cutting a bore in the coal seam. The flexible hose 109 is pulled along by the apparatus, with the hose passing through the whipstock, up the bore and which can be unrolled from a drum 110 on the surface. The flexibility of the hose 109 allows it to pass through a quite tight radius, which in turn allows the whipstock to be compact.

Once the fluid drilling apparatus has cut a desired length of bore, it can be wound back into the arm 107, the arm can be retracted, and the whipstock containing the drilling apparatus can be raised to the surface. The system finds particular use in forming long methane drainage bores in coal.

Figure 10:
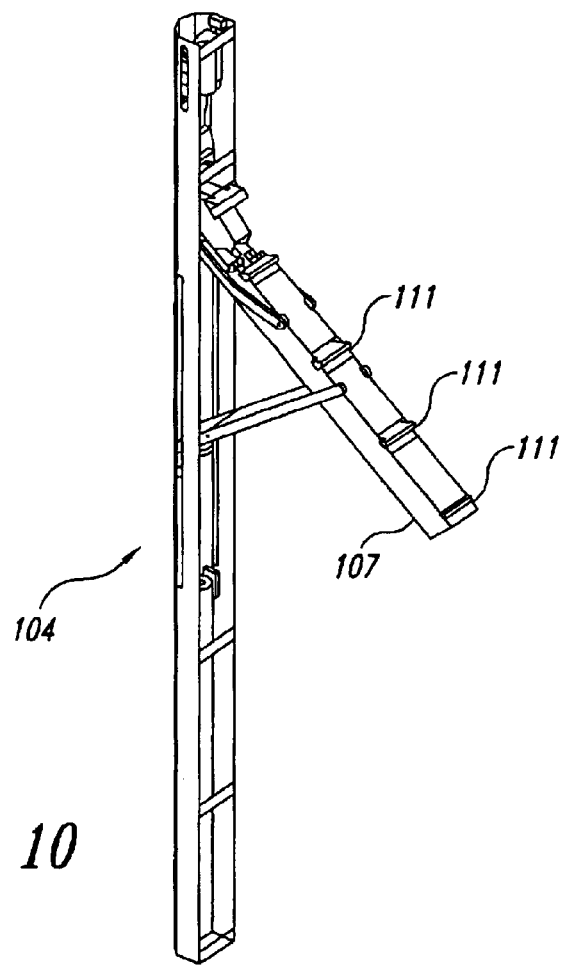
FIG. 10 illustrates a detail of a whipstock assembly of FIG. 9.

FIG. 10 shows a detail of the whipstock apparatus 104. The erectable arm 107 has fluid cutting nozzles 111 to cut a slot in the bore as the arm is erected. It should be appreciated that the fluid drilling system is not limited to use with a whipstock, and can be used alone or with other apparatuses.

Figure 1:
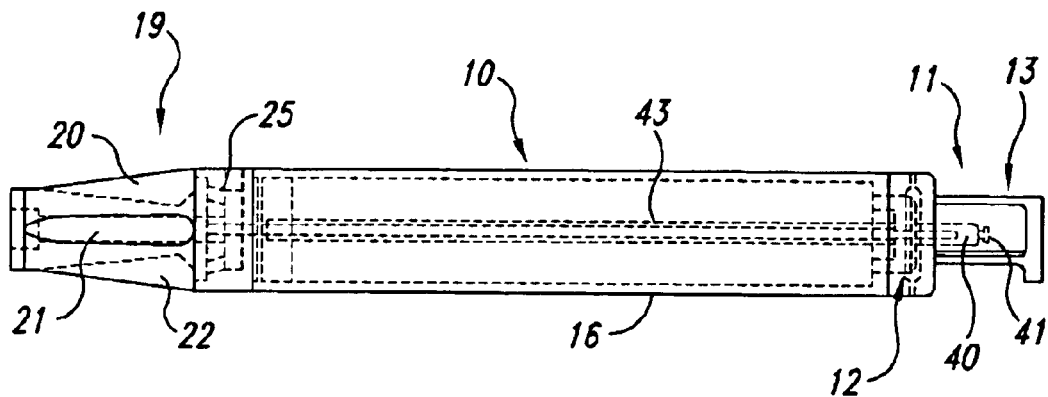
FIG. 1 is an overall side view of a cutting apparatus according to an embodiment of the invention.
Figure 4:
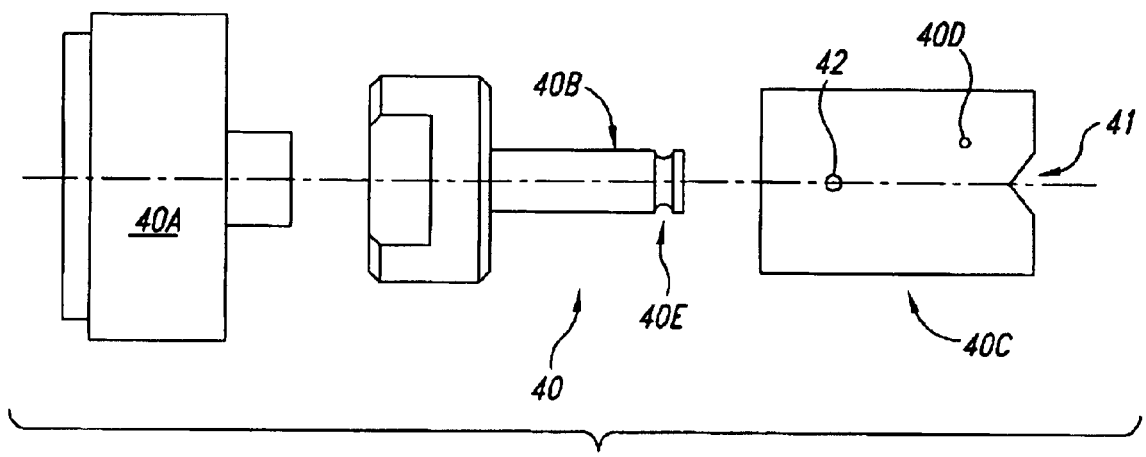
FIG. 4 illustrates the forward fluid cutting nozzles.
Figure 7:
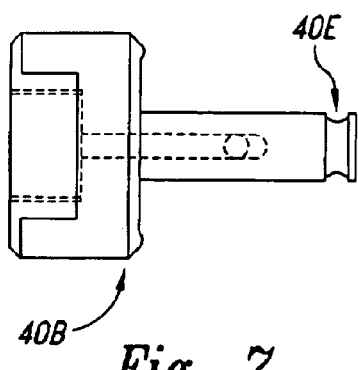
FIG. 7 illustrates part of the forward fluid cutting nozzle.

Referring to FIG. 1, there is illustrated a fluid cutting apparatus 10. Apparatus 10 is formed from a number of separate but interconnectable sub members. The leading sub member 11 comprises a protective housing. The protective housing has a rear substantially hollow tubular portion 12 and a forward cage portion 13. Inside housing 11 is located a Woma FR47 or like type of self-rotating high pressure nozzle assembly 40 which is available commercially (see FIGS. 4 and 7). The nozzle assembly is fitted to a boss 40A and comprises a spindle 40B on which a spinning nozzle 40C sits. Nozzle 40C has forwardly extending cutting jets 41 and side reaming jets 42. Jets 41,42 operate at pressures of between 10000–15000 psi. Nozzle 40C is attached to spindle via a pin 40D which is captured in an annular groove 40E in the spindle.

Cage portion 13 allows the cutting jets and the reaming jets to cut a passageway through solid material (such as a coal seam), with the cage portion protecting the nozzle against damage and stalling.

Figure 3A:
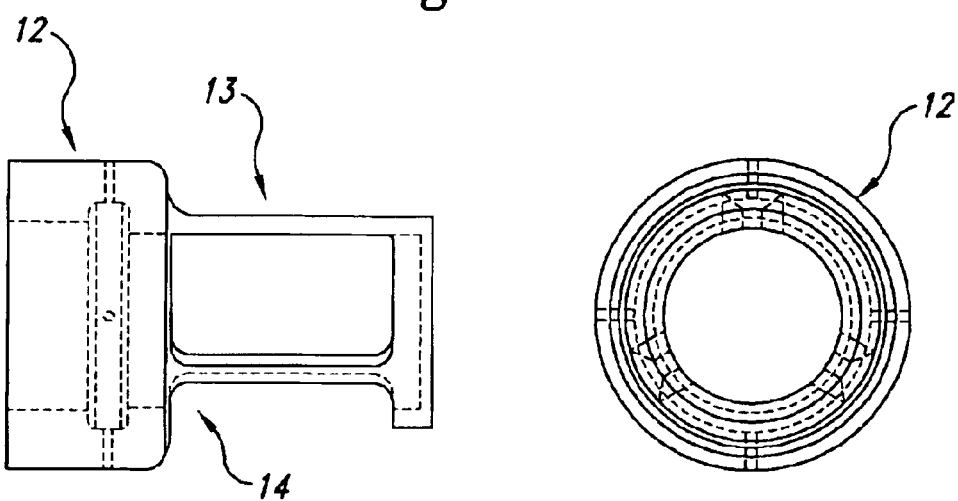
FIGS. 3A and 3B are side and end views of a small stepped leading protective housing.
Figure 3B:
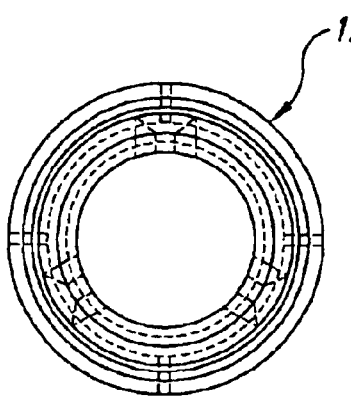

In FIG. 3, cage portion 13 has a step 14 which is positioned immediately behind the reaming nozzles of the Woma unit. Step 14 aims the reaming jets onto protrusions on the borehole wall which catch on the step and prevent the nozzle from advancing. The reaming jets are then able to remove the protrusions and hence will allow the drilling apparatus 10 to advance.

Figure 2:
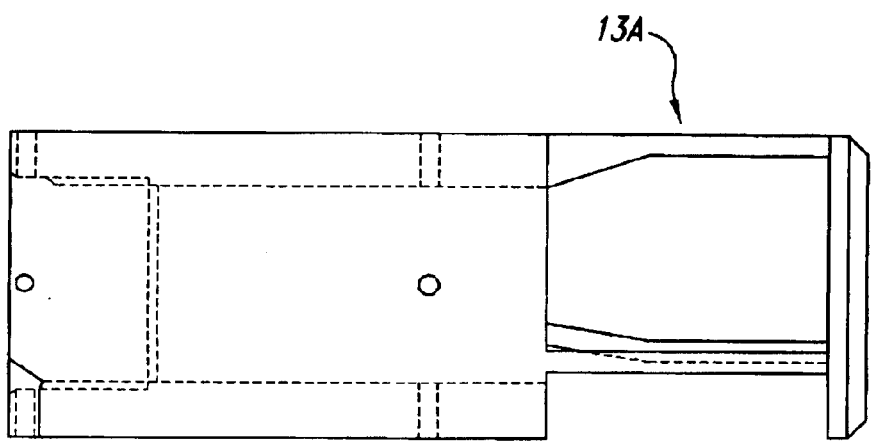
FIG. 2 is a view of a large leading protective housing.

FIG. 2 illustrates a different type of cage portion 13A without the step.

Immediately behind housing 11 is an intermediate sub member 16 which is substantially hollow and can contain sensors, guidance systems and the like. In addition, the sub member is cylindrical in shape, thereby providing a symmetry to the nozzle which assists in drilling straighter holes. The cylindrical shape also effectively reduces the annulus between the nozzle and the borehole wall through which the water and coal cuttings have to pass. High pressure water passes through internal pipe 43 and to the Woma FR47 nozzle. If the borehole diameter gets too small, then this water and cuttings cannot escape past the nozzle fast enough. This leads to an increase in pressure in front of the nozzle to a level at which the nozzle is pushed back against the force of the retro jets. This effectively allows the cutting and reaming jets another opportunity to cut the borehole and increase its diameter. In this manner a more consistent borehole diameter is achieved.

Figure 5:
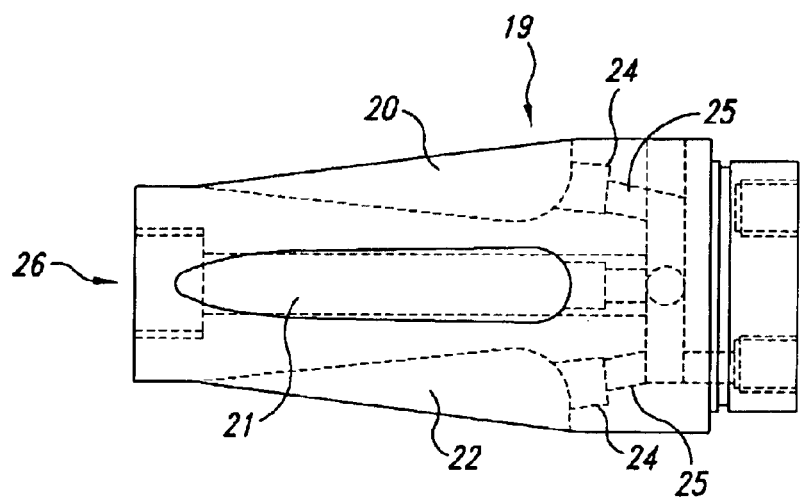
FIG. 5 illustrates the rear retro jet assembly of the cutting apparatus.

Connected to member 16 is a rear retro jet sub member 19 which is more clearly illustrated in FIG. 5. Retro jet sub member 19 has four retro jets 20–23 evenly spaced about a tail end of the member. Each retro jet comprises a channel machined or otherwise formed into the sub member 19. A nozzle (not shown) is positioned in a corresponding socket 24 inside the retro jet sub member 19 and adjacent the channel. The socket and therefore nozzle is in fluid communication with the interior of retro jet sub-member 19 through channels 25. The nozzles are angled at an optimum 5° to the horizontal to clear the attached trailing flexible hose and to provide a good forward thrust to the apparatus. Water passes through the nozzles at 10000–20000 psi. A proportion of high pressure fluid passing into retro jet sub member 19 will therefore pass out through nozzles positioned in the sockets 24 to provide a forward thrust to the drilling apparatus 10. A flexible drilling string (not shown) is attached at the rear portion 26 of retro jet sub member 19. High pressure fluid can pass through the flexible drill string and into and along cutting apparatus 10. The drill string functions as a conduit for the high pressure fluid but is too flexible to provide any meaningful forward thrust to the fluid cutter. The flexibility makes the drill string ideal for passing through tight curves, for instance with a whipstock, and surfactants are not required.

In use, high pressure fluid such as water is passed through the flexible drill string and passes into and through the apparatus 10. The high pressure fluid powers the Woma self-rotating nozzle and also the retro jets.

In a further form, a guidance system for steering the nozzle through the coal seam can be incorporated into the apparatus. The guidance system is designed to provide a continuous and real time indication of the nozzles attitude and position allowing an operator to steer the nozzle by computer control on the surface. The guidance system consists of the following components:

a survey instrument which determines the location of the nozzle in 3-D space, a single core wireline to transmit information between the nozzle and the surface a computer and display monitor which calculate and display information relating to the nozzles trajectory, and steering mechanism located on the nozzle to control the direction of advancement hence maintain a desired trajectory.

The survey instrumentation may consist of a tri-axial array of fluxgate magnetometers and accelerometers. The magnetometers are used to determine the azimuth which the nozzle is pointing relative to magnetic north. The accelerometers are used to determine the inclination of the nozzle along its longitudinal axis, and the clock face orientation of the nozzle.

The output from the magnetometers and accelerometers is collected and processed by a processing chip located in the body of the nozzle. This information is then transmitted to the surface in binary form along the single core wireline. The wireline will be either built into the high pressure hose braiding, attached to the outside of the hose or threaded through the centre of the hose.

On the surface the wireline unit is connected to a computer which downloads the signal from the nozzle, processes the information and calculates the azimuth, inclination and clock face orientation of the nozzle in real time. This information is then displayed on a computer monitor allowing the operator to view the nozzles trajectory and compare this with the desired trajectory.

If the nozzle is deviating from the desired trajectory by a significant amount then the operator can activate the nozzle steering mechanism by using the computer keyboard. The operator enters in the desired change in direction. The computer determines how best to effect the change in direction and a signal is sent down the wireline to the processing chip in the nozzle. The chip activates the steering mechanism and the borehole trajectory is changed.

Figure 6:
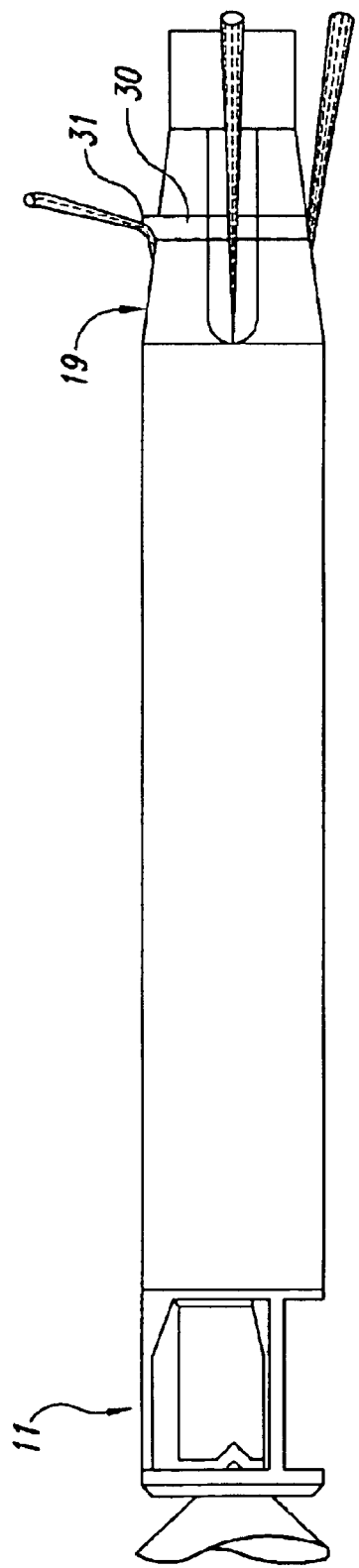
FIG. 6 illustrates the apparatus of FIG. 1 having a deflector mechanism to deflect the retro water jet.

The steering mechanism consists of a slip ring 30 (see FIG. 6) which is mounted in a circumferential groove located behind the retro jets. A protrusion in the form of a plate 31 designed to deflect a retro jet towards the borehole wall is mounted on the slip ring. An actuator stepping motor inside the assembly is used to rotate the slip ring such that the deflector plate is positioned behind the appropriate jet for the desired directional change. The forces generated by deflecting the appropriate retro jet steer the nozzle towards the desired direction.

Figure 8:
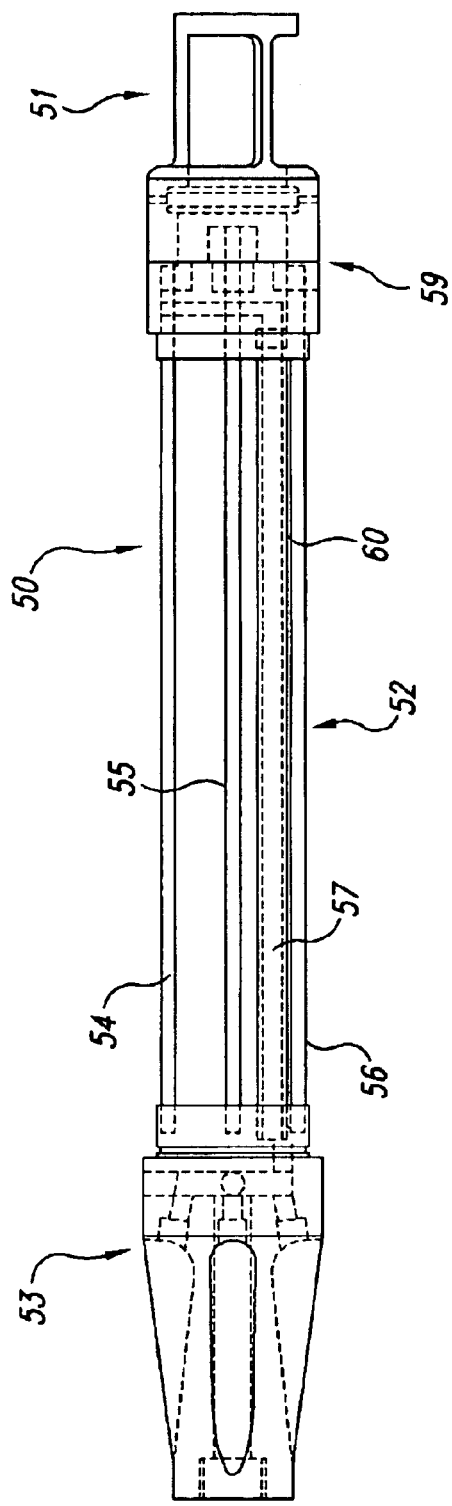
FIG. 8 illustrates a cutting apparatus according to a second embodiment.

Referring to FIG. 8, there is shown a variation in the cutting assembly. The cutting assembly 50 again includes a forward cage portion 51, an intermediate body 52 and a retro jet unit 53, the retro jet unit 53 and the forward cage 51 being substantially the same as described above.

Intermediate body 52 contains four internal stud bars 54–57 which extend longitudinally along and inside intermediate body 52. The stud bars form a support for additional components such as electronic surveying instrumentation. The instrumentation is moulded into epoxy resin and sealed in a canister for protection. The instrument package is mounted in such a manner that it slides onto the four stud bars. The drilling head boss 59 is the cap to the canister and allows attachment of the FR47 nozzle or the like to the assembly. The arrangement is tensioned using nuts which are screwed into the stud bar and the tensioning also seals the assembly together using nylon or similar bushes. Step cage 51 can then be located over the FR47 nozzle. In this arrangement, the internal water pipe 60 is placed to one side along internal body 52 to provide room for the instrument package.

The flexible hose which is attached to the cutting apparatus is a high pressure flexible hose which is sufficiently flexible to allow it to be withdrawn from the bore hole. The hose is also sufficiently flexible to allow it to be deviated by a whipstock. The flexible hose is not designed to act as a pusher to the cutting apparatus, the cutting apparatus being self-advancing via the retro jets. Thus, the flexible hose is different to coiled tubing which can be bent past its elastic limit (for instance past a whipstock), but cannot be retrieved without difficulty and is usually cut-off electrochemically.

In the embodiment, the hose is formed from an inner core being polyoxymethylene and polyamide. Four spiral layers of high tensile steel wire are wrapped around the inner core to provide pressure reinforcement. The outer core is a polyamide. The flexible hose is available commercially under the Polyflex High Pressure Hose™.

In a further form the steering mechanism uses side "thruster" jets to change the direction of the borehole. These jets are activated by solenoid controlled high pressure valves.

In examples, fifty-four non-deflected holes and seven holes with the drill string being deflected through a 0.3 m radius were drilled with the High Pressure Waterjet Drilling Nozzle according to the invention. Various pump pressures, cage types and nozzle orifice sizes were trialled to determine the optimum operating parameters for the nozzle.

On the basis of the results of trials, an optimum combination for drilling is a pump pressure of 115 MPa, a fluid flow rate of 234 liters per minute, and 1.0 mm and 1.2 mm diameter cutting and reaming jets on the Woma FR47 self-rotating nozzle and 1.2 mm diameter orifice for the retro jets. A stepped cage shielding the FR47 nozzle creates a smoother borehole and more consistent borehole diameter.

An example of this nozzle combination was a borehole which penetrated one hundred and ninety-four meters in a total time of 42 minutes when drilling a non-deflected borehole. A further example was a borehole that penetrated one hundred and ninety-two meters in a total time of 97 minutes with the drill string negotiating an ultra-short-radius turn of 0.3 m. Note there is no requirement to stop drilling to couple drill strings with this system. In both the above cases, drilling was ceased because these were the limit of available drill string at that time. The hole diameter was about 110 mm. It is apparent that drilling rates are 10 times that of the known system which uses the weight of the drill string to advance the fluid cutter.

It should be appreciated that various other changes and modifications may be made to the embodiment described without departing from the spirit or scope of the invention.

What is claimed is:

1. A retractable bore drilling apparatus for forming a bore hole in an underground formation, the apparatus comprising:
   a self-advancing drilling head having at least one high pressure fluid cutting nozzle with an at least partially forwardly directed, fluid cutting orifice configured to expel a fluid cutting jet to increase a length of the bore hole;
   an advancing device provided on the drilling head to provide forward movement of the drilling head from a first position in the bore hole to a second position in the bore hole;
   a retractable, flexible, axially unsupported conduit coupled to the drilling head and coupleable to a source of high-pressure fluid, the conduit being axially moveable through the bore hole as the drilling head moves from the first position to the second position; and
   a steering device having at least one jet nozzle configured to direct a jet of fluid, the jet of fluid imparting a biasing force to the apparatus, the biasing force being disposed at a non-zero angle relative to an axis aligned with the length of the bore hole.

2. The apparatus of claim 1 wherein the jet nozzle includes an orifice positioned to direct a jet of fluid at the non-zero angle relative to the axis aligned with the length of the bore hole.

3. The apparatus of claim 1 wherein the fluid cutting orifice is self-rotating.

4. The apparatus of claim 1 wherein the fluid cutting orifice is configured to operate at a pressure of from about 10,000 psi to about 20,000 psi.

5. The apparatus of claim 1 wherein the advancing device includes at least one retro jet positioned to provide forward thrust to the drilling head.

6. The apparatus of claim 1 wherein the advancing device includes at least one retro jet positioned to provide forward thrust to the drilling head and wherein the at least one retro jet is configured to operate at a pressure of from about 10,000 psi to about 20,000 psi.

7. The apparatus of claim 1 wherein the drilling head has a longitudinal axis generally aligned with a direction of forward movement, and wherein the advancing device includes at least one retro jet positioned to provide forward thrust to the drilling head, further wherein the at least one retro jet is configured to expel water at an angle of from about 0 degrees to about 30 degrees relative to the longitudinal axis.

8. The apparatus of claim 1 wherein the at least one high pressure fluid cutting nozzle includes at least one forward cutting jet aperture and at least one side reaming jet aperture.

9. The apparatus of claim 1 wherein the steering device includes a deflecting member, the deflecting member being movable into and out of the jet of fluid passing through the at least one jet nozzle to deflect the jet.

10. The apparatus of claim 1 wherein the steering device includes a deflecting member, the deflecting member being movable into and out of the jet of fluid passing through the at least one jet nozzle to deflect the jet, the deflecting member including a ring rotatable relative to the at least one jet nozzle between a first location with a portion of the ring engaged with the jet of fluid and a second location with the portion disengaged from the jet of fluid.

11. A method for forming a bore hole in an underground formation, comprising:
    disposing a self-advancing drilling head in a bore hole;
    providing high-pressure fluid to the drilling head via a retractable, flexible, axially unsupported conduit coupled to the drilling head;
    increasing a length of the bore hole by expelling a fluid cutting jet from an at least partially forwardly directed, fluid cutting orifice of the drilling head;
    advancing the drilling head through the bore hole from a first position to a second position with an advancing device provided on the drilling head; and
    steering the drilling head by directing a jet of fluid from at least one jet nozzle positioned at least proximate to the drilling head, the jet of fluid imparting a biasing force to the drilling head, the biasing force being disposed at a non-zero angle relative to an axis aligned with the length of the bore hole.

12. The method of claim 11 wherein steering the drilling head includes directing the jet of fluid from an orifice oriented at the non-zero angle relative to the axis aligned with the length of the bore hole.

13. The method of claim 11 wherein steering the drilling head includes moving a deflecting member into and out of the jet of fluid passing through the at least one jet nozzle to deflect the jet.

14. The method of claim 11 wherein steering the drilling head includes moving a deflecting member into and out of the jet of fluid passing through the at least one jet nozzle to deflect the jet, the deflecting member including a ring rotatable relative to the at least one jet nozzle between a first location with a portion of the ring engaged with the jet of fluid and a second location with the portion disengaged from the jet of fluid.

15. The method of claim 11, further comprising removing methane from the bore hole.

16. The method of claim 11 wherein the bore hole is the second of two bore holes and wherein the method further comprises:

drilling a first bore hole from the surface into a subterranean seam;

forming a cavity in the first bore hole adjacent to the seam;

passing a whipstock into the first bore hole and into the cavity; and positioning the drilling head in a selected orientation in the cavity with the whipstock.

17. The method of claim 11, further comprising removing methane through the bore hole.

18. The method of claim 11, further comprising withdrawing the drilling head from the bore hole.

19. The method of claim 11, further comprising spinning a nozzle of the drilling head relative to the conduit.

* * * * *